(12) United States Patent
Kondo et al.

(10) Patent No.: US 10,729,993 B2
(45) Date of Patent: Aug. 4, 2020

(54) FILTRATION FILTER

(71) Applicant: Murata Manufacturing Co., Ltd., Nagaokakyo-shi, Kyoto-fu (JP)

(72) Inventors: Takashi Kondo, Nagaokakyo (JP); Yoshiji Okamoto, Nagaokakyo (JP); Seiji Kamba, Nagaokakyo (JP)

(73) Assignee: MURATA MANUFACTURING CO., LTD., Nagaokakyo-shi, Kyoto-Fu (JP)

( * ) Notice: Subject to any disclaimer, the term of this patent is extended or adjusted under 35 U.S.C. 154(b) by 254 days.

(21) Appl. No.: 15/484,617

(22) Filed: Apr. 11, 2017

(65) Prior Publication Data

US 2017/0216744 A1    Aug. 3, 2017

Related U.S. Application Data

(63) Continuation of application No. PCT/JP2016/066559, filed on Jun. 3, 2016.

(30) Foreign Application Priority Data

Jun. 22, 2015   (JP) .................................. 2015-124772

(51) Int. Cl.
  *B01D 46/00*      (2006.01)
  *B01D 33/01*      (2006.01)
  (Continued)

(52) U.S. Cl.
  CPC ......... *B01D 33/0183* (2013.01); *B01D 33/82* (2013.01); *B01D 39/2027* (2013.01);
  (Continued)

(58) Field of Classification Search
  CPC .... B01D 33/00; B01D 33/0183; B01D 33/82; B01D 33/0041; B01D 63/072;
  (Continued)

(56) References Cited

U.S. PATENT DOCUMENTS

| 4,744,898 A | 5/1988 | Bailey |
| 5,492,551 A * | 2/1996 | Wolfe .................... A41D 13/11 |
| | | 55/496 |

(Continued)

FOREIGN PATENT DOCUMENTS

| JP | S53-18680 U | 2/1978 |
| JP | S61-296192 A | 12/1986 |

(Continued)

OTHER PUBLICATIONS

International Search Report issued in International Application No. PCT/JP2016/066559, dated Sep. 6, 2016.

(Continued)

*Primary Examiner* — T. Bennett McKenzie
(74) *Attorney, Agent, or Firm* — Arent Fox LLP

(57) ABSTRACT

A filtration filter comprises a porous film including a central film portion having a plurality of through holes and an outer edge portion adjacent to the central film portion. The porous film portion lies in a flat plane in the absence of a force being applied to the central portion of the central film portion. A frame holds the outer edge portion of the porous film in such a manner that when a force is applied to the central film portion in a first direction, the central film portion moves in the first direction relative to the flat plane and the outer edge portion moves in a second direction, opposite to the first direction, relative to the flat plane. In this way stresses applied to the porous film during a filtering operation are reduced.

20 Claims, 10 Drawing Sheets

(51) Int. Cl.
| | |
|---|---|
| *B01D 63/08* | (2006.01) |
| *C12M 1/00* | (2006.01) |
| *B01D 33/82* | (2006.01) |
| *B01D 39/20* | (2006.01) |
| *B01D 46/16* | (2006.01) |
| *C12M 1/26* | (2006.01) |
| *B01D 33/00* | (2006.01) |
| *B01D 39/10* | (2006.01) |

(52) U.S. Cl.
CPC ......... *B01D 46/0054* (2013.01); *B01D 46/16* (2013.01); *B01D 63/087* (2013.01); *C12M 33/14* (2013.01); *C12M 47/02* (2013.01); *B01D 33/0041* (2013.01); *B01D 39/10* (2013.01); *B01D 46/0002* (2013.01); *B01D 2201/0415* (2013.01); *B01D 2275/202* (2013.01); *B01D 2275/203* (2013.01); *B01D 2313/025* (2013.01)

(58) Field of Classification Search
CPC .... B01D 46/00; B01D 46/0054; B01D 46/16; B01D 46/0002; B01D 2275/202; B01D 2313/025; B01D 2201/0415; B01D 33/015–0191; B01D 33/0346–0392; B01D 2275/203; B01D 29/0004; B01D 29/0009; B01D 29/0095; B01D 29/01; B01D 29/46; C12M 33/14; C12M 47/02
USPC ........ 435/401; 55/385.4, 406–409, 422, 492, 55/505, 511
See application file for complete search history.

(56) References Cited

U.S. PATENT DOCUMENTS

| | | | | |
|---|---|---|---|---|
| 5,667,699 | A * | 9/1997 | Schlise | B01D 27/106 210/800 |
| 6,033,455 | A * | 3/2000 | Kurashima | A61M 16/105 210/445 |
| 7,546,925 | B1 * | 6/2009 | Zuk, Jr. | B01D 61/18 210/406 |
| 2005/0284116 | A1 * | 12/2005 | Duffy | B01D 46/0001 55/497 |
| 2013/0129565 | A1 * | 5/2013 | Siaw | B01D 46/0028 422/4 |
| 2016/0195458 | A1 | 7/2016 | Kikuhara et al. | |

FOREIGN PATENT DOCUMENTS

| | | |
|---|---|---|
| JP | S62-38213 A | 2/1987 |
| JP | H03-108074 U | 11/1991 |
| JP | H05-9606 U | 2/1993 |
| JP | 2003-103118 A | 4/2003 |
| JP | 2004-202444 A | 7/2004 |
| JP | 2005-270052 A | 10/2005 |
| JP | 2013-32591 A | 7/2013 |
| JP | 2013-202465 A | 10/2013 |
| WO | WO 2015/019889 A1 | 2/2015 |

OTHER PUBLICATIONS

Written Opinion of the International Searching Authority issued in International Application No. PCT/JP2016/066559, dated Sep. 6, 2016.
Japanese Office Action issued for Application No. 2017-524819, dated Jun. 12, 2018.

* cited by examiner

FILTRATION FILTER

CROSS REFERENCE TO RELATED APPLICATIONS

The present application is a continuation of International application No. PCT/JP2016/066559, filed on Jun. 3, 2016, which claims priority to Japanese Patent Application No. 2015-124772, filed on Jun. 22, 2015, the entire contents of each of which are incorporated herein by reference.

TECHNICAL FIELD

The present invention relates to a filtration filter that filters a filtration object in fluid.

BACKGROUND ART

A cell trapping system has recently been disclosed as a usage example of a filter that filters a filtration object in fluid (see, for example, International Publication No. 2015/019889). In this cell trapping system, a filter for trapping cells is fitted in a tensioned state between a lid member and a storage member. Cells are trapped by causing fluid containing the cells to pass through the filter while the filer is in the tensioned state.

SUMMARY OF INVENTION

Because the filter of the forgoing cell trapping system is held in the tensioned state, when the fluid passes through the filter, the filter is broken by stress applied thereto.

The present invention solves this problem by preferably holding the filter in a non-tensioned state and reducing the forces applied to the filter.

In accordance with a preferred embodiment of the invention, the filter includes a porous film including a central film portion having a plurality of through holes and an outer edge portion adjacent to the central film portion. The porous film portion lies in a flat plane in the absence of a force being applied to the central portion of the central film portion. A frame holds the outer edge portion of the porous film in such a manner that when a force is applied to the central film portion in a first direction, the central film portion moves in the first direction relative to the flat plane and the outer edge portion moves in a second direction, opposite to the first direction, relative to the flat plane.

The porous film is preferably made of metal. The outer edge portion can have a holding hole and the frame can have a first projection extending through the holding hole. The diameter and/or shape of the holding hole allows the outer edge portion to move in the second direction. The diameter of the first projection is preferably larger than a diameter of the holding hole and has a conical shape.

In an alternative embodiment, the frame has a recess that receives the outer edge portion. A dimension of the recess in a direction perpendicular to the flat plane is larger than a thickness of the outer edge portion in the direction perpendicular to the flat plane. The recess defines a fulcrum about which the porous film pivots when the force is applied to the central film portion. The frame preferably prevents the porous film from moving along the plane when it is bent by the force applied to the central film portion.

The recess preferably has first and second opposed surfaces which are spaced apart from one another in a direction perpendicular to the flat plane. The central film portion is preferably circular in shape and has a center. The length of the first and second opposed surfaces, as measured along a direction parallel to the flat plane, can be the same or different.

In one embodiment, the first and second flat surfaces terminate at first and second circular openings, respectively, the first circular opening being larger than the second circular opening.

In another embodiment, the frame includes one or more support surfaces located at respective positions spaced from flat plane, each support surface limiting the amount that the central film portion can move in response to the application of an external force to the central film portion in the direction of the support surfaces. The one more support surfaces can include a plurality of projections.

In this embodiment, central film portion is preferably circular in shape and has a center. Each of the respective projections is a respective distance from the center of the central film portion. Each of the respective projections is also spaced from the flat plane by a respective distance as measured in a direction perpendicular to the flat plane. The distance that a respective projection is spaced from the flat plane decreases as a function of the distance of the respective projection from the center of the central film portion such that respective projections which are closer to the center of the central film portion are spaced further away from the flat plane than respective projections which are further from the center of the central film portion.

It is possible for the one or more support surfaces to come into contact with a crosspiece of the central film portion when a fluid to be filtered passes through the central film portion.

According to the present invention, it is possible to provide a filter that can suppress breakage of the filter by relaxing the stress applied to the filter.

DESCRIPTION OF PREFERRED EMBODIMENTS

Figure 1:
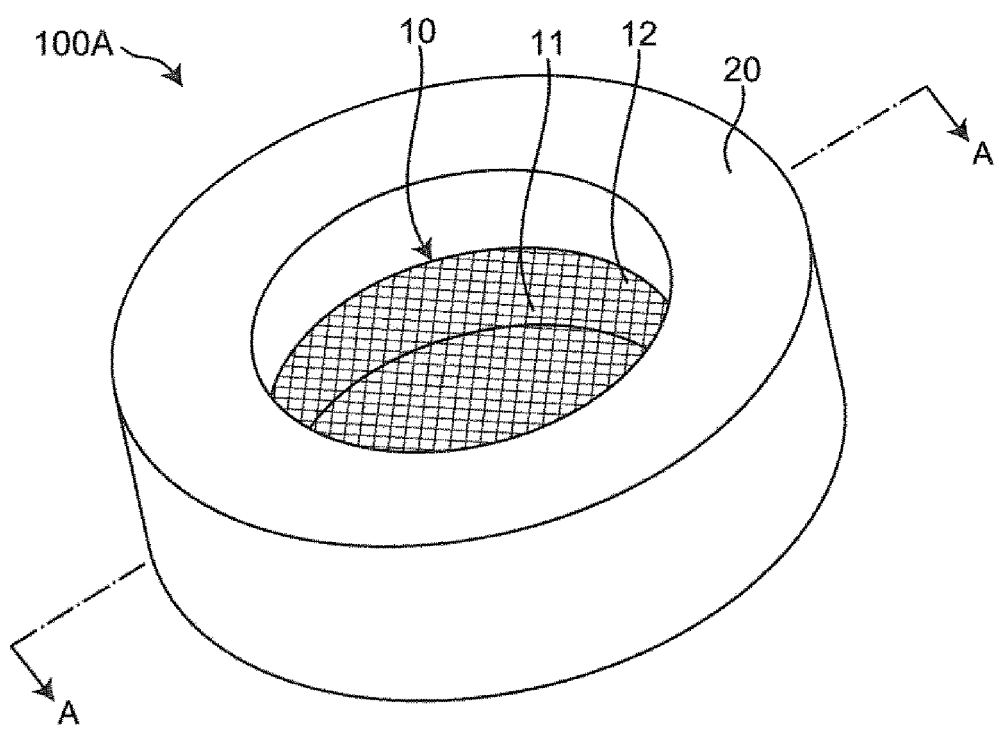
FIG. 1 is a schematic structural view of a filtration filter according to a first embodiment of the present invention.

Embodiments of the present invention will be described below with reference to the accompanying drawings. In the drawings, elements are exaggeratedly illustrated for easy explanation.

First Embodiment

[Overall Structure]

Figure 2:
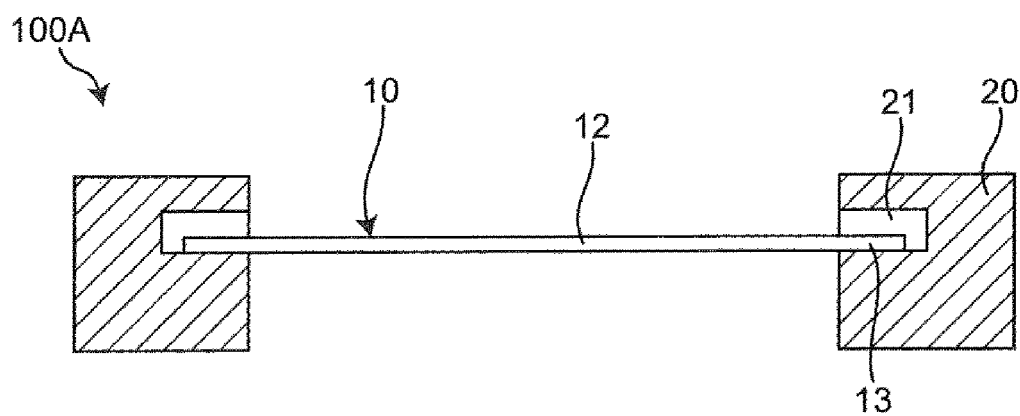
FIG. 2 is a cross-sectional view of the filtration filter, taken along line A-A of FIG. 1.

FIG. 1 is a schematic view of a filtration filter 100A according to a first embodiment of the present invention. FIG. 2 is a cross-sectional view of the filtration filter 100A, taken along line A-A of FIG. 1. As illustrated in FIGS. 1 and 2, the filtration filter 100A includes a porous film 10 that separates a filtration object contained in fluid which is passed through the porous film, and a frame 20 that holds an edge portion of the porous film 10. The porous film 10 is composed of a film portion 12 having a plurality of through holes 11, and an edge portion 13 adjacent to the film portion 12. In the first embodiment, the edge portion 13 (FIG. 2) of the porous film 10 is held by a recess 21 of the frame 20 so that it moves in the thickness direction of the porous film 10.

Fluid containing a filtration object is passed through the porous film 10 and the filtration filter 100A separates the filtration object from the fluid. In this description, the term "filtration object" refers to an object to be filtered by the porous film 10. In the first embodiment, a biological substance is preferably used as the filtration object, and liquid is preferably used as the fluid.

In this description, the term "biological substance" refers to a substance derived from organisms, for example, a cell (eukaryote), a bacterium (*eubacterium*), and a virus. Examples of the cell (eukaryote) include an ovum, a sperm, an induced pluripotent stem cell (iPS cell), an ES cell, a stem cell, a mesenchymal stem cell, a mononuclear cell, a single cell, a cell mass, a floating cell, an adherent cell, a nerve cell, a white blood cell, a lymphocyte, a regeneration medical cell, a self-cell, a cancer cell, a circulating tumor cell (CTC), HL-60, HELA, and germs. Examples of the bacterium (*eubacterium*) include a gram-positive bacterium, a gram-negative bacterium, an *escherichia coli*, and a *tubercle bacillus*. Examples of the virus include a DNA virus, an RNA virus, a rotavirus, an (avian) influenza virus, a yellow fever virus, a dengue fever virus, an encephalitis virus, a hemorrhagic fever virus, and an immunodeficiency virus. In the first embodiment, the filtration filter 100A is excellent in separating, especially, an induced pluripotent stem cell (iPS cell), an ES cell, a stem cell, and a circulating tumor cell (CTC) from the liquid.

<Porous Film>

The porous film 10 is a porous film that separates a biological substance from a fluid. The porous film 10 is preferably a metallic thin film composed of a film portion 12 having a plurality of through holes 11 and an edge portion 13 adjacent to the film portion 12. As illustrated in FIG. 1, in the first embodiment, the porous film 10 is formed by a circular metal mesh and includes a pair of opposed principal surfaces and a plurality of through holes 11 penetrating both principal surfaces of the film portion 12. The plurality of through holes 11 may be periodically arranged all over the principal surfaces of the film portion 12. For example, the porous film 10 may be made of Ni, the dimensions of the porous film 10 may be 6 mm in diameter and 1.2 μm in thickness. The thickness of the porous film 10 is preferably within the range of 0.5 to 100 μm. The void ratio of the porous film is preferably within the range of 10% to 90%. The void ratio (i.e., the ratio of the area of the holes to the area of the principal surface (including the holes) of the porous film. is more preferably within the range of 20% to 50%. This structure can allow the porous film 10 to be easily bent when the fluid containing the filtration object passes through the porous film 10 and can restrict the porous film 10 from being bent when the fluid does not pass through the porous film 10. The material of the porous film 10 may be gold, silver, copper, platinum, iron, nickel, chromium, stainless steel, palladium, titanium, or an alloy of these materials. In particular, when the biological substance is trapped, gold, nickel, stainless steel, or titanium is preferably used from the viewpoint of biocompatibility with the biological substance. The material of the porous film 10 may be an elastic material having a Young's modulus of 1 GP or more.

Figure 3:
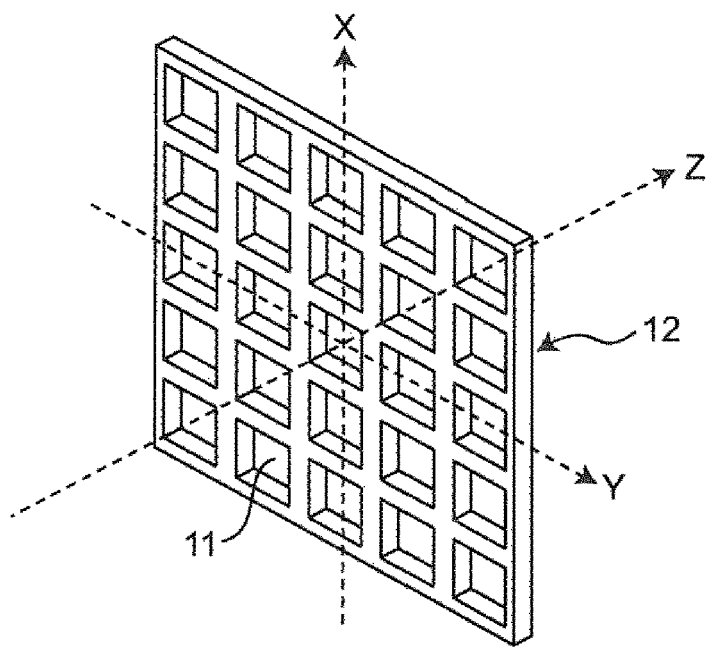
FIG. 3 is a schematic view of a part of a film portion in a porous film according to the first embodiment of the present invention.
Figure 4:
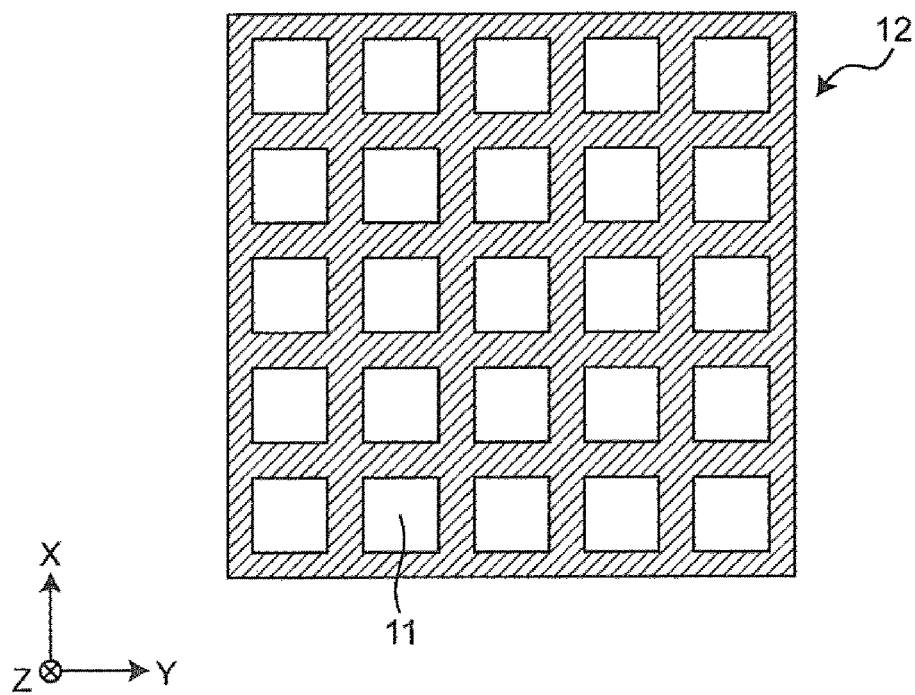
FIG. 4 is a schematic view of the part of the film portion of FIG. 3, when viewed from the thickness direction.

FIG. 3 is a schematic structural view of a part of the film portion 12 formed by a two-dimensional periodic structure. In FIG. 3, the X, Y, and Z directions respectively represent the longitudinal direction, the lateral direction, and the thickness direction of the structure. FIG. 4 illustrates the part of the film portion 12 shown in FIG. 3, when viewed from the Z-direction. As illustrated in FIGS. 3 and 4, the film portion 12 may be a plate-shaped structure (i.e., a flat structure) in which a plurality of through holes 11 are arranged at regular intervals and in a matrix. The film portion 12 is a plate-shaped structure in which a plurality of square through holes 11 are provided when viewed from the Z-direction on the principal surface side. The plural through holes 11 are provided at regular intervals in two arrangement directions parallel to the sides of squares, that is, in the X-direction and the Y-direction in FIG. 3. The shape of the through holes 11 is not limited to the square shape, but may be, for example, a rectangular shape, a circular shape, or an elliptic shape. Also, the arrangement of the holes is not limited to the square lattice arrangement, but may be, for example, a rectangular arrangement in which the intervals are not equal between the two arrangement directions as long as the arrangement is the quadrangular arrangement, or may be, for example, a triangular lattice arrangement or a quasiperiodic arrangement.

The shape and dimensions of the through holes 11 in the film portion 12 are appropriately designed according to the size and shape of the biological (or other) substance to be filtered. For example, the through holes 11 are square when viewed from the principal surface side of the film portion 12, that is, viewed from the Z-direction, and are designed to be within the range of 0.1 to 500 μm in length and within the range of 0.1 to 500 μm in width. The interval between the through holes 11 is, for example, within the range of 1 to 10 times of the size of the through holes 11, and more preferably 3 times or less of the size of the through holes 11. Alternatively, the aperture ratio is preferably 10% or more.

<Frame>

The frame 20 holds the edge portion 13 of the porous film 10. As illustrated in FIG. 1, in the first embodiment, the frame 20 is formed by an annular member. As illustrated in FIG. 2, the frame 20 has a recess 21 opening toward the porous film 10 to hold the edge portion 13 of the porous film 10. The dimension of the recess 21 in the thickness direction of the frame 20 is designed to be larger than the thickness of the edge portion 13. Also, the dimension of the recess 21 in the thickness direction of the frame 20 is designed so that a distal end of the edge portion 13 of the porous film 10 comes into contact with an upper inner wall of the recess 21 and a part of a lower surface of the edge portion 13 comes into contact with a lower inner wall of the recess 21 when the fluid passes through the porous film 10. By thus designing the dimensions of the recess 21, the upper inner wall and the lower inner wall of the recess 21 can hold the edge portion 13 of the porous film 10 when the film portion 12 is bent.

For example, the dimension of the recess 21 in the thickness direction of the frame 20 is designed to be larger than 100% and smaller than or equal to 500% of the thickness of the edge portion 13. More preferably, the dimension of the recess 21 in the thickness direction of the frame 20 is designed to be within the range of 200% to 400% of the thickness of the edge portion 13. This can form a gap that permits the edge portion 13 of the porous film 10 to move in the thickness direction of the porous film 10 while at the same time preventing the porous film 10 from coming out of the frame 20. In this way, the frame 20 holds the edge portion 13 of the porous film 10 in a state in which the porous film 10 is not fixed and no tension is applied thereto. The frame 20 does not always need to hold the entire circumference of the edge portion 13 of the porous film 10, and for example, may hold two opposed portions of the edge portion 13 or hold a plurality of spaced, preferably equally spaced, portions of the edge portion 13.

In the first embodiment, the frame 20 has first and second frames (these frames are shown combined as a single from in FIGS. 1 and 2). In the frame 20 of the first embodiment, after the porous film 10 is inserted into the first frame, the second frame is fitted to the first frame. This allows the porous film 10 to be held inside the frame 20.

[Motion of Filtration Filter During Passage of Liquid]

Figure 5:
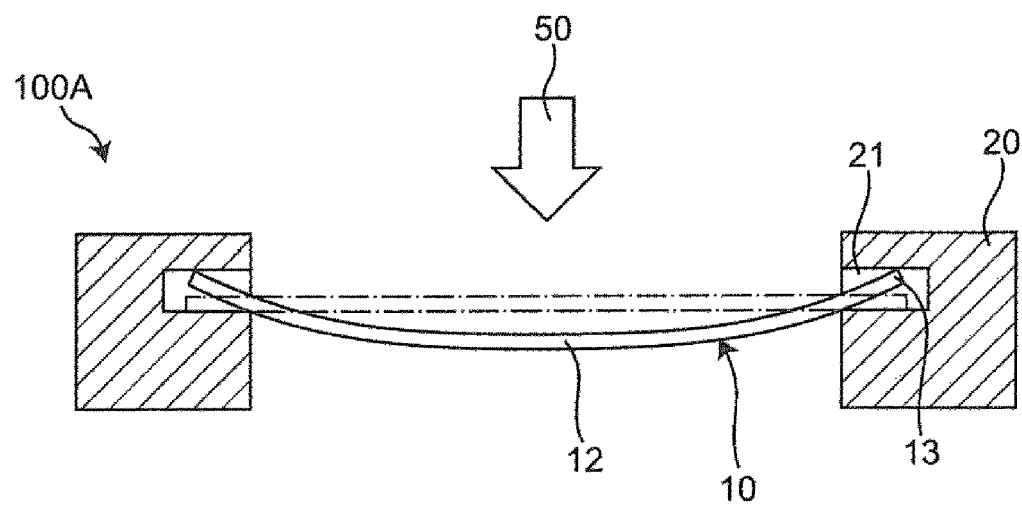
FIG. 5 illustrates the motion of the filtration filter according to the first embodiment of the present invention during passage of liquid.

FIG. 5 illustrates the motion of the filtration filter 100A during passage of liquid through the filtration filter 100A. A white arrow denoted by reference numeral 50 in FIG. 5 shows the flow of the liquid from the upstream side to the downstream side of the filtration filter 100A. As illustrated in FIG. 5, in the filtration filter 100A, when liquid containing a biological substance passes through the porous film 10 in the direction 50, stress in the direction 50 is applied to a center portion of the film portion 12. Because the pivot (fulcrum) defined at the bottom inner edges of the recess 21, the edge portion 13 of the porous film 10 moves in a direction opposite from the direction 50 inside the recess 21. Specifically, the edge portion 13 of the porous film 10 is curved (bent) and raised in the direction opposite from the direction 50 at an angle to the center portion of the film portion 12. Since the edge portion 13 of the porous film 10 can thus move in the thickness direction of the porous film 10 without being fixed, the center portion of the porous film 10 can be bent in the direction 50 opposite from the direction in which the edge portion 13 moves.

The motion of the edge portion 13 of the porous film 10 is restricted by the upper wall surfaces of the recess 21. Specifically, when the edge portion 13 of the porous film 10 is raised in the direction opposite from the direction 50, the distal end of the edge portion 13 of the porous film 10 comes into contact with an upper inner wall of the recess 21, and another part of the edge portion 13 comes into contact with an inner edge of the lower inner wall of the recess 21. That is, the distal end of the edge portion 13 is supported by the upper inner wall of the recess 21, whereas the part of the lower surface of the edge portion 13 is supported by the lower inner wall of the recess 21. For this reason, the edge portion 13 of the porous film 10 does not come out of the recess 21, but is held by the frame 20. The amount that the film portion 12 can bend depends on the dimension of the recess 21 in the thickness direction of the frame 20. Specifically, the bending amount depends on the dimension of the gap between the upper wall of the recess 21 and the edge portion 13. As this gap increases, the amount the edge portion 13 of the porous film 10 can move when the liquid to be filtered passes through the film portion 10 increases. during passage of the liquid increases. Hence, the bending amount of the film portion 12 increases.

In this way, when the liquid passes through the filtration filter 100A, the film portion 12 is bent in the direction 50 in which the liquid flows. This can reduce the force of the liquid in the direction perpendicular to the film portion 12, and relax the stress applied to the film portion 12. That is, in the filtration filter 100A, the force in the direction 50, in which the liquid flows, can be released from the film portion 12 and the stress applied to the film portion 12 can be relaxed by bending the film portion 12. Also, when the liquid does not pass through the filtration filter 100A, the film portion 12 is held in an unbent state by the frame 20, as illustrated in FIG. 2.

As described above, in the filtration filter 100A, when the liquid containing the biological substance passes through the porous film 10, the biological substance is separated from the liquid while the film portion 12 is bent and the stress applied to the film portion 12 is reduced.

[Effects]

According to the filtration filter 100A of the first embodiment, the following effects can be achieved.

In the filtration filter 100A, the recess 21 of the frame 20 holds the edge portion 13 of the porous film 10 so that the edge portion 13 moves in the thickness direction of the porous film 10. That is, the frame 20 does not fix the porous film 10, but holds the porous film 10 under no tension. According to this structure, the film portion 12 can be bent in the direction 50 in which the liquid flows when the liquid passes through the filtration filter 100A. As a result, when the liquid passes through the filtration filter 100A, the stress applied to the film portion 12 can be relaxed by bending the film portion 12, and this can suppress breakage of the film portion 12.

In the filtration filter 100A, the dimension of the recess 21 in the thickness direction of the frame 20 is designed to be larger than the thickness of the edge portion 13 of the porous film 10. This structure can form, inside the recess 21, the gap that permits the edge portion 13 of the porous film 10 to move in the thickness direction of the porous film 10. Since the edge portion 13 of the porous film 10 moves in the thickness direction of the porous film 10 inside this gap, the film portion 12 can be moved in the direction opposite from the direction in which the edge portion 13 moves. This allows the film portion 12 to be bent reliably. Also, in the filtration filter 100A, the bending amount of the film portion 12 can be controlled by adjusting the dimension of the recess 21 in the thickness direction of the frame 20.

In the filtration filter 100A, when the liquid does not pass through the porous film 10, the film portion 12 is held in an unbent state. In this way, in the filtration filter 100A, the film portion 12 is bent when the liquid passes. This can enhance handleability of the user. For example, when the filtration filter 100A is mounted in a filtration device, the user can mount the filtration filter 100A while holding only the frame 20. At this time, the film portion 12 is held in an unbent state. For this reason, the filtration filter 100A can suppress the user from erroneously touching the film portion 12 and can reduce the risk of soiling the film portion 12, compared with the filtration filter in which the film portion 12 is always bent.

The porous film 10 is preferably made of metal. This structure can further suppress breakage of the porous film 10. Also, when the liquid passes through the film portion 12, since the through holes 11 hardly deform, the biological substance can be suppressed from passing through the film portion 12 owing to deformation of the through holes 11.

While the terms "filtration object" and "fluid" have been respectively described as, for example, the biological substance and the liquid in the first embodiment, they are not limited thereto. The fluid may be gas. The filtration object may be, for example, particulate matter (PM 10, SPM, or PM 2.5).

While the metallic thin film is used as the porous film 10 in the first embodiment, the porous film 10 is not limited thereto. For example, the porous film 10 may be a film formed, for example, by a membrane, filter paper, or non-woven fabric.

Figure 6:
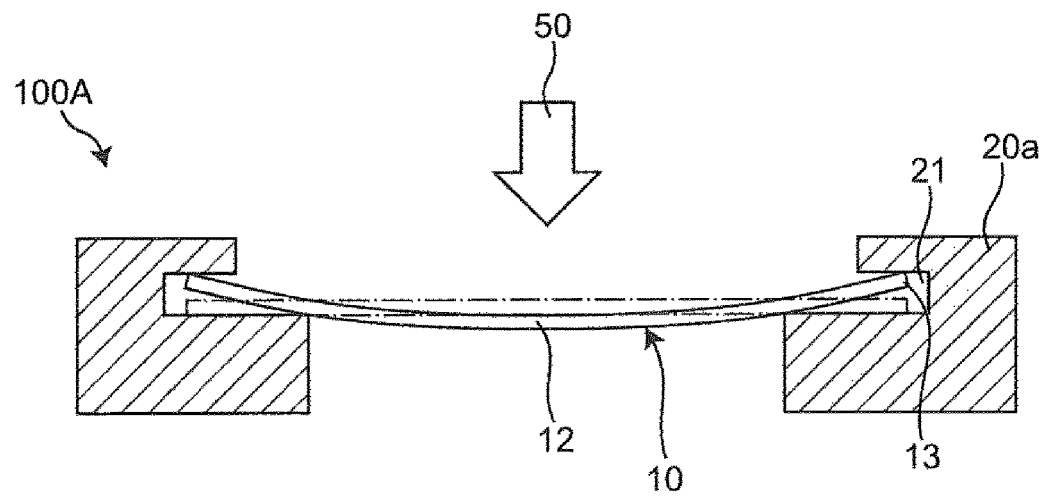
FIG. 6 illustrates the motion of a modification of the filtration filter according to the first embodiment of the present invention during passage of the liquid.

FIG. 6 illustrates the motion of a modification of the filtration filter 100A according to the first embodiment. As illustrated in FIG. 6, a frame 20a may be structured in a manner such that the area of a lower inner wall of a recess 21 is larger than the area of an upper inner wall of the recess 21. This structure increases the area in which a lower surface of an edge portion 13 of a porous film 10 is in contact with the lower inner wall of the recess 21. Hence, when a film portion 12 is bent, the lower surface of the edge portion 13 is easily supported by the lower inner wall of the recess 21.

While the frame 20 has two frames in the first embodiment, the invention is not so limited. For example, the frame 20 may have two or more frames. Alternatively, the frame 20 may be formed by a single component.

Second Embodiment

[Overall Structure]

A filtration filter according to a second embodiment of the present invention will be described with reference to FIG. 7.

Figure 7:
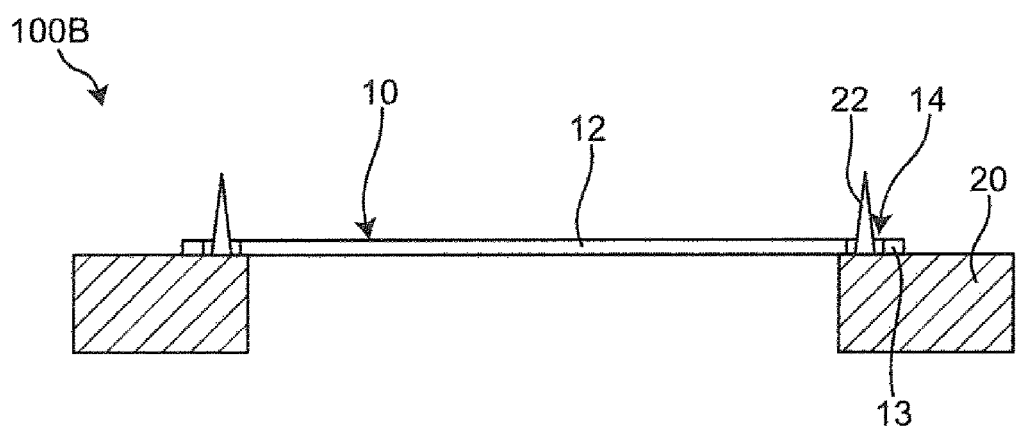
FIG. 7 is a schematic structural view of a filtration filter according to a second embodiment of the present invention.

FIG. 7 illustrates a schematic structure of a filtration filter 100B according to a second embodiment. In the second embodiment, differences from the first embodiment will be mainly described. In the second embodiment, structures identical or equivalent to those of the first embodiment are denoted by the same reference numerals. Also, in the second embodiment, descriptions overlapping with those of the first embodiment are skipped.

As illustrated in FIG. 7, the filtration filter 100B of the second embodiment is different from the filtration filter 100A of the first embodiment in the structure for holding a porous film 10. Specifically, an edge portion 13 of the porous film 10 has a holding hole 14, and a frame 20 has a projection 22 instead of the recess 21.

<Holding Hole>

The holding hole 14 is a hole in which the projection 22 is to be inserted, and is provided in the edge portion 13 of the porous film 10. The holding hole 14 communicates between two opposed principal surfaces of the porous film 10. The holding hole 14 preferably has a circular shape, when viewed from the principal surface side of the porous film 10. The diameter of the holding hole 14 is designed to be larger than the diameter of the projection 22. In the second embodiment, for example, a plurality of holding holes 14 are equally spaced on the concentric edge portion 13 of the porous film 10, when viewed from the principal surface side of the porous film 10 formed by a circular metal mesh.

<Projection>

The projection 22 holds the edge portion 13 of the porous film 10 by being inserted in the holding hole 14 of the porous film 10. The projection 22 projects from an upper surface of the frame 20 in the thickness direction of the frame 20. In the second embodiment, for example, a plurality of projections 22 are provided at positions corresponding to the holding holes 14 of the porous film 10.

The projections 22 may be, for example, conical pins. The diameter of the projections 22 is designed to be smaller than the diameter of the holding holes 14. That is, the diameter of the holding holes 14 is designed to be larger than the diameter of the projections 22, and for example, the diameter of the holding holes 14 is designed to be larger than 100% and smaller than or equal to 200% of the diameter of the projections 22. Thus, when the projections 22 are inserted in the holding holes 14, gaps that allow the edge portion 13 of the porous film 10 to move in the thickness direction of the porous film 10 can be formed between inner walls of the holding holes 14 and the projections 22. Also, the height of the projections 22 in the thickness direction of the frame 20 is designed at such a height that the holding holes 14 do not come out of the projections 22. The height of the projections 22 is appropriately determined according to the dimensions such as the diameter of the holding holes 14 and the diameter of the porous film 10.

[Motion of Filtration Filter During Passage of Liquid]

Figure 8:
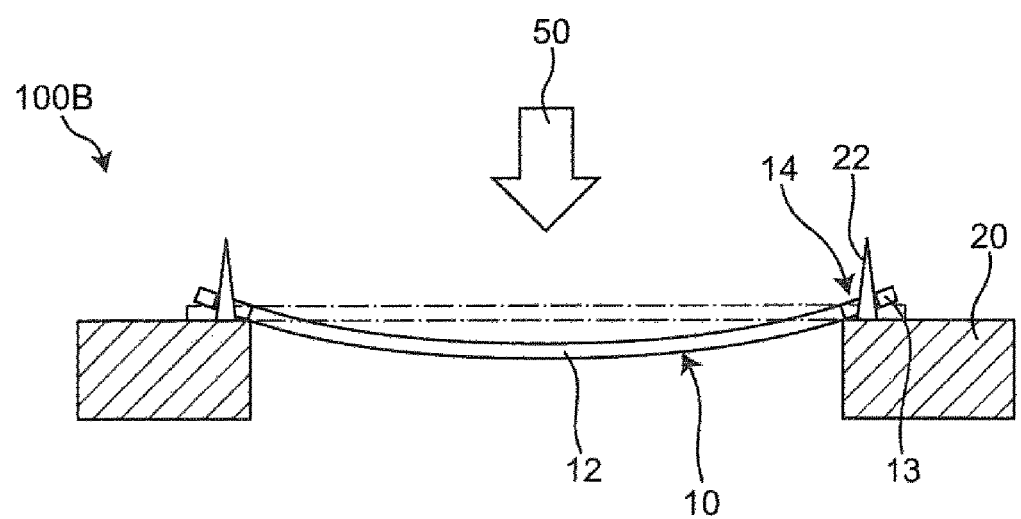
FIG. 8 illustrates the filtration filter according to the second embodiment of the present invention during passage of liquid.

FIG. 8 illustrates the motion of the filtration filter 100B when a liquid passes there through. A white arrow denoted by reference numeral 50 in FIG. 8 shows the flow of liquid from the upstream side to the downstream side of the filtration filter. As illustrated in FIG. 8, in the filtration filter 100B, when liquid containing a biological substance passes through the porous film 10 in the direction 50, stress in the direction 50 is applied to a center portion of the film portion 12. At this time, the edge portion 13 of the porous film 10 moves in a direction opposite from the direction 50 along outer walls of the projections 22 inserted in the holding holes 14. Specifically, the edge portion 13 of the porous film 10 is curved and raised in the direction opposite from the direction 50 at an angle to the center portion of the film portion 12. Since the edge portion 13 of the porous film 10 can thus move in the thickness direction of the porous film 10 without being fixed, the center portion of the film portion 12 can be bent in the direction 50.

When the edge portion 13 of the porous film 10 moves in the direction opposite from the direction 50, the inner walls of the holding holes 14 are caught by outer walls of the projections 22 and the edge portion 13 of the porous film 10 is held with an angle by the frame 20. In this way, the projections 22 function as fall-preventing members for the porous film 10 while restricting the movement of the edge portion 13. The bending amount of the film portion 12 depends on the diameter of the holding holes 14. Specifically, the bending amount depends on the dimensions of the gaps between the inner walls of the holding holes 14 and the outer walls of the projections 22. When the gaps increase, the moving amount of the edge portion 13 of the porous film 10 during passage of the liquid increases. Hence, the bending amount of the film portion 12 increases.

[Effects]

According to the filtration filter 100B of the second embodiment, the following effects can be achieved.

In the filtration filter 100B, the frame 20 holds the porous film 10 with the projections 22 thereof inserted in the holding holes 14 provided in the edge portion 13 of the porous film 10. Also, since the diameter of the holding holes 14 is larger than the diameter of the projections 22, when the projections 22 are inserted in the holding holes 14, gaps can be formed between the inner walls of the holding holes 14 and the projections 22. Accordingly, when the liquid passes through the filtration filter 100B, the edge portion 13 of the porous film 10 is moved with an angle in the thickness direction of the porous film 10 and this can bend the film portion 12 in the direction 50 in which the liquid flows. As a result, when the liquid passes through the filtration filter 100B, the stress applied to the film portion 12 can be relaxed by bending of the film portion 12 and this can suppress breakage of the film portion 12.

In the filtration filter 100B, the bending amount of the film portion 12 can be controlled by adjusting the diameter of the holding holes 14 and the diameter of the projections 22.

While the holding holes 14 have a circular shape when viewed from the principal surface side of the porous film 10 in the second embodiment, the shape is not limited thereto. It is only necessary that the holding holes 14 should have such a shape to permit insertion of the projections 22. The holding holes 14 may have an arbitrary shape such as a triangular shape, a quadrangular shape, a trapezoidal shape, or an elliptic shape. Alternatively, the holding holes 14 may be slots extending toward the center portion of the porous film 10. When the holding holes 14 are formed as slots extending toward the center portion of the porous film 10, the movement of the edge portion 13 of the porous film 10 in the directions other than the thickness direction, for example, the movement in the circumferential direction of the porous film 10 can be restricted.

While the projections 22 are conical pins, for example, in the second embodiment, the shape is not limited thereto. The projections 22 can have any shape as long as they can hold the porous film 10 by being inserted in the holding holes 14 of the porous film 10 while permitting the edge portion 13 of the porous film 10 to move in the thickness direction of the porous film 10. For example, the projections 22 may be shaped like a triangular prism, a quadrangular prism, or a circular column.

While the projections 22 are provided on the upper surface of the frame 20 in the second embodiment, the structure is not limited thereto. For example, the projections 22 may be provided inside the recess 21 of the first embodiment. According to this structure, since the recess 21 and the projections 22 can hold the edge portion 13 of the porous film 10, the porous film 10 can be held while more reliably bending the film portion 12.

Third Embodiment

[Overall Structure]

A filtration filter according to a third embodiment of the present invention will be described with reference to FIGS. 9 and 10.

Figure 9:
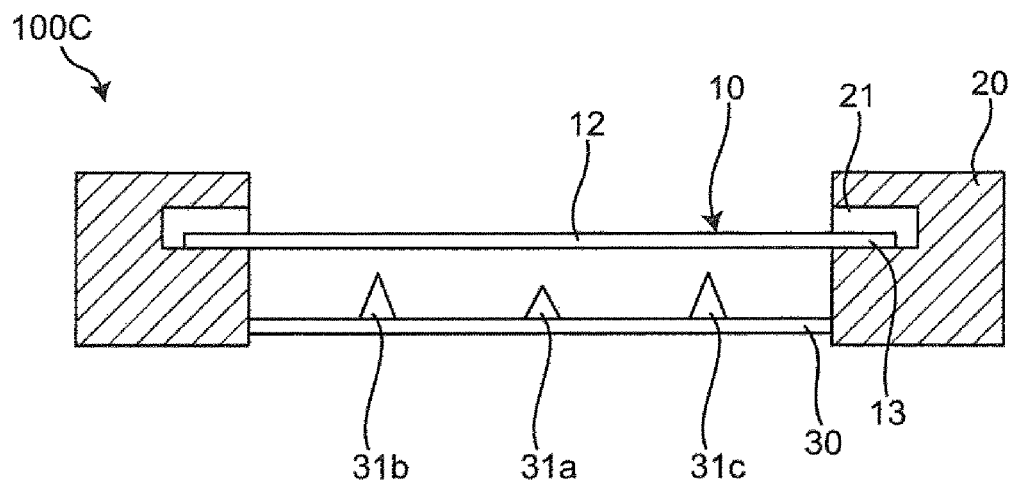
FIG. 9 is a schematic structural view of a filtration filter according to a third embodiment of the present invention.

FIG. 9 illustrates a schematic structure of a filtration filter 100C according to the third embodiment. FIG. 10 illustrates a schematic structure of a frame 20 in the third embodiment. In FIG. 10, the porous film 10 is not illustrated for easy explanation.

Differences of the third embodiment from the first embodiment will be mainly described. In the third embodiment, structures identical or equivalent to those of the first embodiment are denoted by the same reference numerals. Also, in the third embodiment, descriptions overlapping with those of the first embodiment will be skipped.

Figure 10:
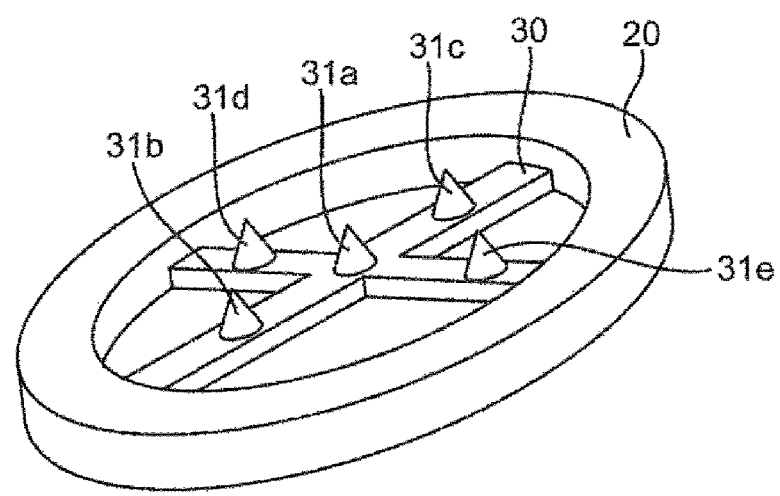
FIG. 10 is a schematic structural view of a frame in the third embodiment of the present invention.

As illustrated in FIGS. 9 and 10, the filtration filter 100C of the third embodiment is different from the filtration filter 100A of the first embodiment in having a support part 30. The support part 30 supports a bent film portion 12 when liquid passes through the filtration filter 100C. As illustrated in FIGS. 9 and 10, the support part 30 is disposed at a position spaced from the principal surface of the film portion 12 in the thickness direction. Specifically, the support part 30 is provided on an inner wall of a frame 20, and is disposed on the downstream side of the film portion 12 relative to the flow of fluid through the filtration filter. The support part 30 has two plate-shaped members, and is disposed so that the members intersect at a position corresponding to a center portion of the film portion 12. On a surface of the support part 30 on the side of the film portion 12, a plurality of projections 31a, 31b, 31c, 31d, and 31e are provided.

As illustrated in FIG. 10, the projection 31a is disposed at the position corresponding to the center portion of the film portion 12, that is, at the position where the two plate-shaped members intersect. The projections 31b, 31c, 31d, and 31e are disposed at positions at a predetermined distance from the projection 31a. The plurality of projections 31a to 31e are arranged to be in contact with the film portion 12 along the shape of the bent film portion 12. Specifically, as illustrated in FIG. 9, the plurality of projections 31a to 31e are designed so that the distance between distal ends of the projections 31a to 31e and the lower principal surface of the film portion 12 decreases from the center portion toward the outer side portion of the film portion 12. That is, the height of the projection 31a in the thickness direction of the film portion 12 is designed to be smaller than the height of the projections 31b, 31c, 31d, and 31e. The plurality of projections 31a to 31e may be conical pins.

[Motion of Filtration Filter During Passage of Liquid]

Figure 11:
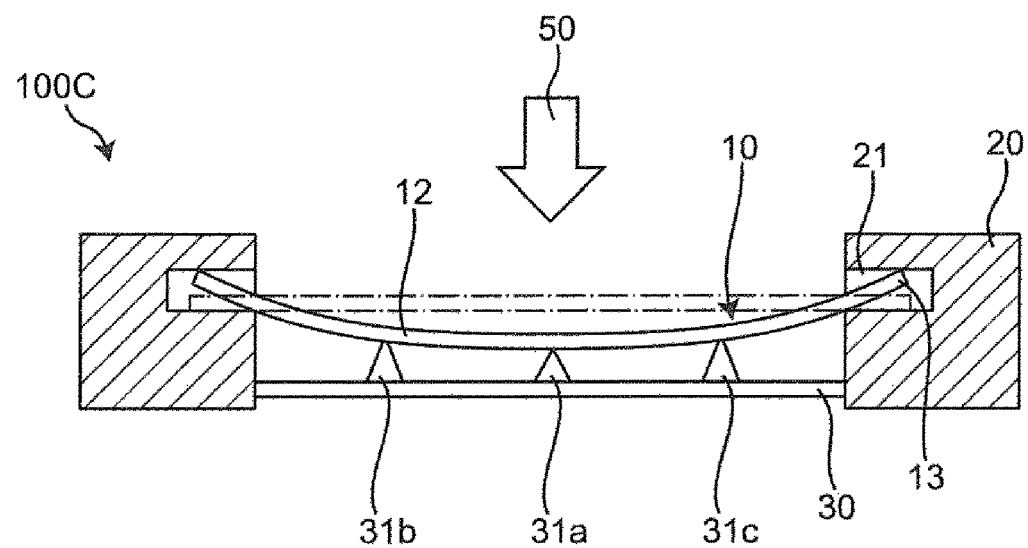
FIG. 11 illustrates the filtration filter according to the third embodiment of the present invention during passage of liquid.

FIG. 11 illustrates the motion of the filtration filter 100C while a liquid (more generally a fluid) is passing through there through. In FIG. 11, a white arrow denoted by reference numeral 50 in FIG. 11 shows the flow of liquid from the upstream side to the downstream side of the filtration filter. As illustrated in FIG. 11, when liquid containing a biological substance passes through the film portion 12 of the filtration filter 100C in the direction 50, stress in the direction 50 is applied to the center portion of the film portion 12, and the center portion of the film portion 12 is bent in the direction 50. The bent film portion 12 comes into contact with the distal ends of the plurality of projections 31a to 31e in the support part 30. In this way, the support part 30 suppresses excessive bending of the film portion 12.

The plurality of projections 31a to 31e of the support part 30 preferably come into contact with a crosspiece of the film portion 12 when the fluid passes through the film portion 12. The crosspiece of the film portion 12 refers to a portion of the film portion 12 where the through holes 11 are not provided. According to this structure, the plurality of projections 31a to 31e of the support part 30 come into contact with the crosspiece of the film portion 12 and this can restrict bending of the film portion 12 without hindering the flow of the fluid.

[Effects]

According to the filtration filter 100C of the third embodiment, the following effects can be achieved.

In the filtration filter 100C, the frame 20 is provided with the support part 30 that supports the bent film portion 12 when the liquid passes there through. Also, in the support part 30, the plurality of projections 31a to 31e projecting toward the film portion 12 are arranged to come into contact with the bent film portion 12. This structure restricts excessive bending of the film portion 12 during passage of the liquid. As a result, stress concentration can be restricted from being caused by excessive bending of the film portion 12. Further, since the plurality of projections 31a to 31e are provided on the surface of the support part 30, the support part 30 can support the film portion 12 while dispersing the stress applied to the film portion 12.

In the filtration filter 100C, the plurality of projections 31a to 31e are designed so that the distance between the distal ends of the projections and the principal surface of the film portion 12 decreases from the center portion toward the outer side portion of the film portion 12. According to this structure, the plurality of projections 31a to 31e come into contact with the film portion 12 along the shape of the film portion 12 bent when the liquid passes. For this reason, the projections 31a to 31e can more equally disperse the stress applied to the film portion 12. As a result, the filtration filter 100C can reliably suppress breakage of the film portion 12.

By using the conical pins as the plurality of projections 31a to 31e, the film portion 12 can be supported without hindering the flow of the liquid.

Figure 12:
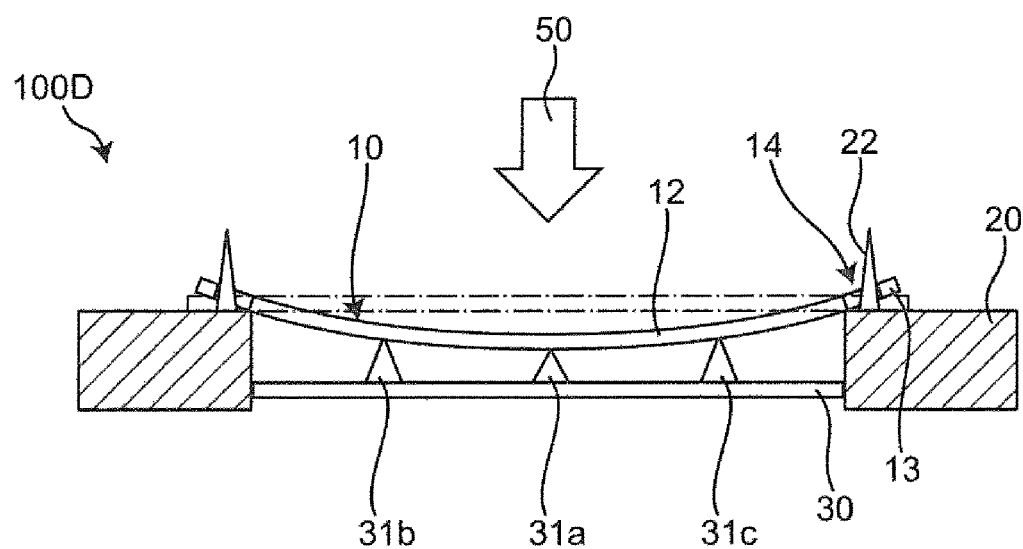
FIG. 12 is a schematic structural view of another filtration filter according to the third embodiment of the present invention.

While the support part 30 is added to the structure of the first embodiment in the structure of the third embodiment, the structure is not so limited. FIG. 12 illustrates a schematic structure of another filtration filter according to the third embodiment. For example, as illustrated in FIG. 12, the support part 30 may be added to the structure of the second embodiment.

Figure 13:
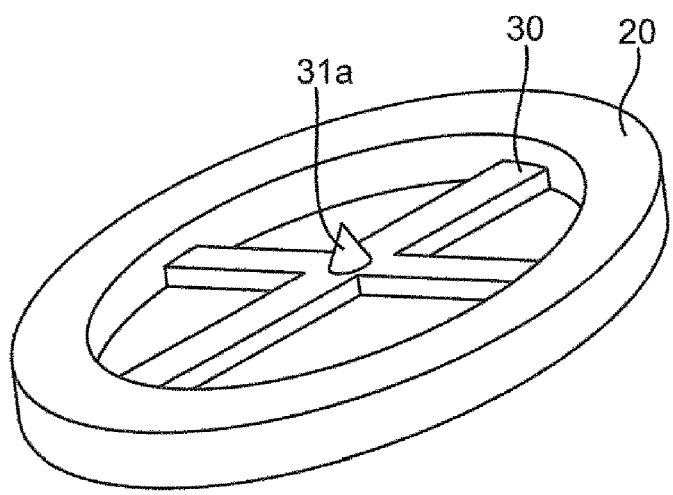
FIG. 13 is a schematic structural view of another frame in the third embodiment of the present invention.
Figure 14A:
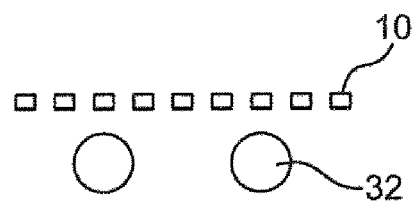
FIG. 14A illustrates a modification of a support part in the third embodiment of the present invention.
Figure 14B:
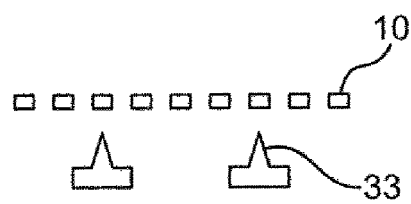
FIG. 14B illustrates a modification of the support part in the third embodiment of the present invention.
Figure 14C:
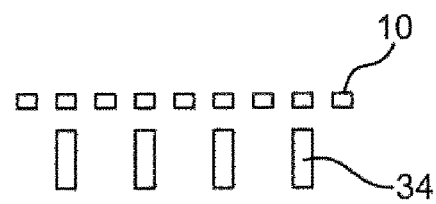
FIG. 14C illustrates a modification of the support part in the third embodiment of the present invention.
Figure 14D:
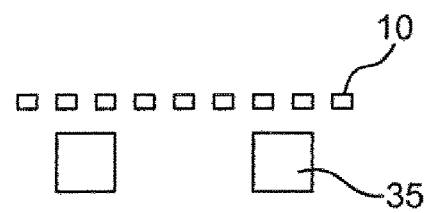
FIG. 14D illustrates a modification of the support part in the third embodiment of the present invention.
Figure 14E:
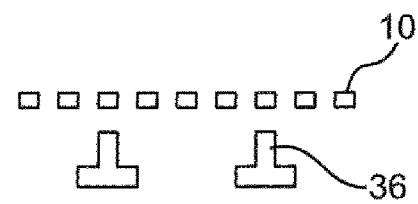
FIG. 14E illustrates a modification of the support part in the third embodiment of the present invention.

While the support part 30 has the plurality of projections 31a to 31e in the third embodiment, the structure is not so limited. The number of projections can be set at an arbitrary number, for example, according to the size of the film portion 12. For example, the support part 30 may be structured to have no projection, to have only one projection, or to have more than five projections. FIG. 13 illustrates a schematic structure of another frame 20 in the third embodiment. As illustrated in FIG. 13, for example, the support part 30 may have one projection 31a at a position corresponding to the center portion of the film portion 12. By reducing the number of projections on the support part 30, the flow of the liquid can be suppressed from being hindered by the projections.

While the illustrated projections 31a to 31e are shaped like conical pins, the structure is not so limited. The support part 30 can have any shape that can come into contact with the film portion 12 bent during passage of the liquid. FIGS. 14A to 14E illustrate modifications of the support part in the third embodiment. As illustrated in FIGS. 14A to 14E, the support part 30 may be a circular support part 32, an acute triangular support part 33, a rectangular support part 34, a square support part 35, or an inverse-T shaped support part 36, in a cross section taken along the direction in which the fluid flows. To firmly support the film portion 12, a support part having a large surface area in contact with the principal surface of the film portion 12, for example, the support part 32 and the support part 35 respectively having the circular cross section and the square cross section illustrated in FIGS. 14A and 14D may be used. To suppress the support part from hindering the flow of the fluid, a support part having a small surface area in contact with the principal surface of the film portion 12, for example, the support part 33, the support part 34, and the support part 36 respectively having the acute triangular cross section, the rectangular cross section, and the inverse-T shaped cross section illustrated in FIGS. 14B, 14C, and 14E may be used.

While the present invention has been sufficiently described in conjunction with the preferred embodiments with reference to the accompanying drawings, various modifications and alterations are obvious to those skilled in the art. It should be understood that such modifications and alterations are included in the present invention without departing from the scope of the present invention described in the accompanying claims.

INDUSTRIAL APPLICABILITY

The present invention relates to the filtration filter, and is excellent in suppressing breakage of the filtration filter when the fluid passes therethrough. For example, the invention can be used for medical diagnosis by taking out cells from a biospecimen and used for environmental measures by trapping PM 2.5 existing in the air.

REFERENCE SIGNS LIST

10: porous film
11: through hole
12: film portion
13: edge portion
14: holding hole
20: frame
21: recess
22: projection
30: support part
31: projection
32, 33, 34, 35, 36: support part
50: direction
100A, 100B, 100C: filtration filter

The invention claimed is:
1. A filter, comprising:
a porous film including a central film portion having a plurality of through holes and an outer edge portion adjacent to the central film portion, the porous film, including both the central film portion and the outer edge portion, lying in a flat plane in the absence of a force having a component which is perpendicular to the flat plane being applied to the central film portion; and
a frame that holds the outer edge portion of the porous film in such a manner that when a force having a component which is perpendicular to the flat plane is applied to the central film portion, the central film portion moves in a first direction relative to the flat plane and the outer edge portion moves in a second direction, opposite to the first direction, relative to the flat plane, an outermost edge of the outer edge portion being unsupported and free to move up and down relative to the flat plane.
2. The filter according to claim 1, wherein the porous film is made of metal.

3. The filter according to claim 1, wherein:
the outer edge portion has a holding hole;
the frame has a first projection extending through the holding hole; and
a diameter and/or shape of the holding hole allow the outer edge portion to move in the second direction.

4. The filter according to claim 3, wherein the diameter of the first projection is larger than a diameter of the holding hole.

5. The filter according to claim 4, wherein the first projection has a conical shape.

6. The filter according to claim 1, wherein:
the frame has a recess that receives the outer edge portion; and
a dimension of the recess in a direction perpendicular to the flat plane is larger than a thickness of the outer edge portion in the direction perpendicular to the flat plane.

7. The filter according to claim 6, wherein the recess defines a fulcrum about which the porous film pivots when the force is applied to the central film portion.

8. The filter according to claim 1, wherein the frame prevents the porous film from moving along the flat plane when it is bent by the force applied to the central film portion.

9. The filter according to claim 6, wherein the recess has first and second opposed surfaces which lie parallel to the flat plane and are spaced apart front one another in a direction perpendicular to the flat plane.

10. The filter according to claim 9, wherein:
the central film portion is circular in shape; and
the length of the first and second opposed surfaces, as measured along a direction parallel to the flat plane, are different.

11. The filter according to claim 10, wherein the first and second opposed surfaces terminate at first and second circular openings, respectively, the first circular opening being larger than the second circular opening.

12. The filter according to claim 1, wherein the frame includes one or more support surfaces located at respective positions spaced from the flat plane, each support surface limiting the amount that the central film portion can move in response to the application of an external force to the central film portion in the direction of the support surfaces.

13. The filter according to claim 12, wherein the one or more support surfaces comprise a plurality of projections.

14. The filter according to claim 13, wherein:
the central film portion is circular in shape and has a center;
each of the respective projections is a respective distance from the center of the central film portion;
each of the respective projections is spaced from the flat plane by a respective distance as measured in a direction perpendicular to the flat plane; and
the distance that a respective projection is spaced from the flat plane decreases as a function of the distance of the respective projection from the center of the central film portion such that respective projections which are closer to the center of the central film portion are spaced further away from the flat plane than respective projections which are further from the center of the central film portion.

15. The filter according to claim 12, wherein the one or more support surfaces come into contact with a crosspiece of the central film portion when a fluid to be filtered passes through the central film portion.

16. The filter according to claim 1, wherein an outermost edge the porous film moves in the second direction when the central film portion moves in the first direction.

17. The filter according to claim 1, wherein the outermost edge extends around the entire outer edge portion of the porous film.

18. The filter according to claim 17, wherein the outermost edge of the porous film is circular in shape.

19. The filter according to claim 18, wherein the outer edge portion of the porous film located radially inward of the outermost edge portion pivots around an edge of the frame when a force having a component which is perpendicular to the flat plane is applied to the central film portion.

20. The filter according to claim 19, wherein, when the central portion of the porous film moves in a first direction, the outermost edge moves in a second direction, opposite to the first direction.

* * * * *